(12) United States Patent
Ehret et al.

(10) Patent No.: US 7,936,785 B2
(45) Date of Patent: *May 3, 2011

(54) APPARATUS FOR GENERATING AND INTERPRETING A DATA STREAM MODIFIED IN ACCORDANCE WITH THE IMPORTANCE OF THE DATA

(75) Inventors: Andreas Ehret, Nuremberg (DE); Holger Hoerich, Nuremberg (DE); Michael Schug, Erlangen (DE); Andreas Schneider, Nuremberg (DE)

(73) Assignees: Coding Technologies AB, Stockholm (SE); SK Telecom Co., Ltd., Seoul (KR)

( * ) Notice: Subject to any disclaimer, the term of this patent is extended or adjusted under 35 U.S.C. 154(b) by 995 days.

This patent is subject to a terminal disclaimer.

(21) Appl. No.: 11/611,311

(22) Filed: Dec. 15, 2006

(65) Prior Publication Data

US 2007/0140359 A1    Jun. 21, 2007

Related U.S. Application Data

(60) Provisional application No. 60/750,897, filed on Dec. 16, 2005.

(30) Foreign Application Priority Data

May 30, 2006    (WO) .................. PCT/EP2006/005140

(51) Int. Cl.
*H04J 3/24* (2006.01)
(52) U.S. Cl. .................. 370/473; 280/294; 280/295

(58) Field of Classification Search .................. 370/473, 370/535; 714/798; 709/231; 704/230; 375/240.08, 375/240.27; 386/96; 710/305
See application file for complete search history.

(56) References Cited

U.S. PATENT DOCUMENTS

| | | | |
|---|---|---|---|
| 5,742,623 A * | 4/1998 | Nuber et al. .................. | 714/798 |
| 6,460,086 B1 | 10/2002 | Swaminathan et al. | |
| 6,631,484 B1 * | 10/2003 | Born .............................. | 710/305 |
| 6,728,924 B1 | 4/2004 | Lou et al. | |

(Continued)

FOREIGN PATENT DOCUMENTS

| | | |
|---|---|---|
| EP | 1 021 038 | 7/2000 |
| EP | 1021039 | 7/2000 |

OTHER PUBLICATIONS

MPEG-4 Video Frequently Asked Questions; http://www.chiariglione.org/mpeg/faq/mp4-vid/mp4-vid.htm; Mar. 2000; pp. 1.

(Continued)

*Primary Examiner* — Dang T Ton
*Assistant Examiner* — Lionel Preval
(74) *Attorney, Agent, or Firm* — Thomas, Kayden, Horstemeyer & Risley, LLP

(57) ABSTRACT

An apparatus for generating a data stream having a series of segments using data organized in subsequent data frames, a data frame having more important and less important data. It comprises a packetiser for packetising data from a data frame into the series of segments having a first segment and a second segment, where the packetiser is operative to packetise the data of the frame so that a starting point of the more important data coincides with a starting point of the first segment and an information block adder for adding a first information block to the first segment.

37 Claims, 4 Drawing Sheets

U.S. PATENT DOCUMENTS

| | | | |
|---|---|---|---|
| 6,873,629 B2 * | 3/2005 | Morris | 370/535 |
| 7,606,928 B2 | 10/2009 | Wang et al. | |
| 2002/0018010 A1 | 2/2002 | Le | |
| 2002/0031123 A1 | 3/2002 | Watanabe et al. | |
| 2002/0118749 A1 * | 8/2002 | Gentric et al. | 375/240.08 |
| 2002/0165710 A1 * | 11/2002 | Ojanpera | 704/230 |
| 2003/0091339 A1 * | 5/2003 | Isozaki | 386/96 |
| 2003/0133441 A1 | 7/2003 | Watanabe et al. | |
| 2004/0162911 A1 * | 8/2004 | Sperschneider et al. | 709/231 |
| 2004/0184369 A1 | 9/2004 | Herre et al. | |
| 2006/0062312 A1 * | 3/2006 | Lee et al. | 375/240.27 |

OTHER PUBLICATIONS

Series H: Audiovisual and Multimedis Systems: Infrastructure of Audiovisual Services—Transmission Multiplexing and Synchronization; Mar. 2004; pp. 9 and 19-20.

M. Handley, C. Perkins; "Guidelines for Writers of RTP Payload Format Specifications;" Dec. 1999; pp. 1-11.

Kretschmer, Basso, Civanlar, Quackenbush, and Snyder; "RTP Payload Format for MPEG-2 and MPEG-4 AAC Streams;" Jul. 2001; pp. 1-10.

La Baule; "Overview of the MPEG-4 Standard;" Oct. 2000; pp. 1-60.

English language translation of the Notification of Examination dated Nov. 24, 2009.

English language translation of abstract of TW I242957.

Taiwanese language office action dated Feb. 4, 2010.

English language translation of office action.

Meer; "RTP Payload Format for Transport of MPEG-4 Elementary Streams;" Philips Electronics; Nov. 2003; pp. 1-43.

International Telecommunication Union; "Series H; Audiovisual and Multimedia Systems; Infrastructure of Audiovisual Services—Transmission Mutliplexing and Synchronization;" Mar. 2004, pp. i-49.

* cited by examiner

101: channel with fixed sized segments of length d
102: data stream
d1, d2, d3,...: date frames 500: data stream
510, 520,...: segments
505, 515, 525: information blocks
545, 565, 575: pointer
530, 535, 550, 560, 570: code words
540: start / entry point 600: information block
610, 620...680: bits of the information block

APPARATUS FOR GENERATING AND INTERPRETING A DATA STREAM MODIFIED IN ACCORDANCE WITH THE IMPORTANCE OF THE DATA

CROSS-REFERENCE TO RELATED APPLICATION

The present application claims priority to U.S. Provisional patent application No. 60/750,897, filed Dec. 16, 2005, and to PCT Application number PCT/EP2006/005140, filed May 30, 2006, both of which are incorporated herein by reference.

BACKGROUND OF THE INVENTION

The present invention relates to the transmission of data over error prone channels with fixed length data packages. It is especially suitable for perceptual audio coding.

Modern audio coding methods such as e.g. MPEG Layer 3, MPEG AAC or MPEG HE-AAC (MPEG=moving picture experts group, HE-AAC=high efficient advanced audio coding) are capable of reducing the data rate of digital audio signals by means of exploiting some psycho-acoustical properties of the human ear. Hereby a block of a fixed number of audio samples, called frame, is encoded to a compressed bit stream representation of this fixed time interval. The compressed audio frame will be transformed back to an audio sample representation in the decoder. Since the difficulty to encode an audio signal may vary for different audio frames, the well-known bit reservoir technique allows exchanging bits between the frames. Although the overall bit rate is constant, as a consequence the length of the frames in the bit stream is variable. The encoded frame has a part with side information containing essential information for the decoder to interpret the compressed data, followed by the compressed spectral data.

For transmission, the compressed audio frame has to be embedded into a transport format such as e.g. the ADTS (ADTS=audio data transport stream) or LOAS (LOAS=low overhead audio stream) transport formal for MPEG AAC. If there are errors in the transmission, it will be possible for the decoder to re-synchronize, due to sync-words, on the bit stream after the loss of one or more frames. Since in modern audio codecs, spectral data and parts of the side information is often entropy coded with code words of variable length such as e.g. Huffman coding in MPEG AAC, a single bit error is often sufficient for the decoder having to discard the whole frame and to mute the output signal or use some error concealment technique, e.g. noise insertion or interpolation between intact frames or a combination thereof. If longer regions of errors occur during the transmission, the decoder is still able to re-synchronize on the bit stream, but it does not have information about the number of frames that have been lost. In addition to the concealment of multiple frames, this can lead to audible time shift on the audio played back by the decoder or dropouts due to buffer over- or under-runs. Especially over error-prone channels, to keep a high quality of the transmitted audio signal, it is extremely important to have a sophisticated error-management available.

The invention is especially suited for the transmission over error prone channels with fixed length data segments. Because of the variable length of the frames, such as compressed audio frames, a new frame for a well-known transport format such as e.g. the already mentioned ADTS or LOAS formats usually starts at arbitrary positions of the fixed length data segment. Therefore, in case such a segment gets lost, which contains data of two consecutive frames, both frames will be corrupt and must be replaced by an error concealment strategy of the decoder.

SUMMARY OF THE INVENTION

In the following description, a data frame refers to a frame of data from e.g. an audio codec such as MPEG-4 High Efficiency AAC. This data frame can have varying length in bits, i.e. varying size. Furthermore, the data frame is divided into several data segments of constant size. There can be one or multiple constant size segments for every data frame. Within the data segments of constant size, data entities are present. These correspond to e.g. Huffman code-words representing e.g. spectral data of the encoded signal. The data segments contain several data entities. Some are complete data entities, referred to as interpretable data entities, and some are data entity fragments, which are in-complete data entities not interpretable on their own.

Furthermore, in the following description, the transport protocol header or the information block, refers to elements that contain information to be able to identify the boundary of an exemplary variable length audio data frame. In further embodiments, it comprises information to make a single data segment self-contained, i.e. the information describes the range of the e.g. audio spectrum a certain data segment covers, and where in the data segment the interpretable data entity begins, without depending on valid reception of another data segment.

The present invention provides a method for efficient transport of packaged data with variable length framing over error prone channels with fixed length data segments. In a preferred embodiment it is used for transmitting compressed audio data in form of audio frames of variable length, in which it comprises the following steps.

At an encoder: compressed audio data frames of arbitrary size are mapped into fixed size data segments for a transmission over an error prone channel; a transport protocol header or an information block is inserted at the beginning of each data segment; the transport protocol header or the information block contains information to be able to identify the boundaries of a variable length audio data frame and in further embodiments to identify where in the data segment the interpretable data entity begins; the above transport protocol header information or information block can be coded in a very efficient manner down to a single byte. This is achieved by exploiting certain parameter inter-dependencies such that only cases with highest likelihood are coded.

At a decoder: a transport handler receives the segments and the information whether the transmission was successful or not, it strips off the transport protocol header or the information block and concatenates the data of each received frame which is then passed to the decoder; for the case of data segment losses, the transport protocol header or the information block contains information to reconstruct the number of lost audio frames which allows for a correct time synchronization; for the case of data segment losses, the transport protocol header or the information block contains information to make a single data segment self-contained, i.e. the information describes the range of the audio spectrum a certain data segment covers, without depending on valid reception of another data segment. If this information is passed to the decoder it can apply partial concealment methods It is an object of the present invention to provide a concept for obtaining an improved audio quality even in situations of transmitting audio data over error prone channels.

In accordance with a first aspect of the invention, this object is achieved by an apparatus comprising a packetiser for packetising data from a data frame into a series of segments having a first segment and a second segment, where the packetiser is operative to packetise the data of the frame so that a starting point of the more important data coincides with a starting point of the first segment and an information block adder for adding a first information block to the first segment. The apparatus comprises furthermore an information block adder for adding a first information block to the first segment.

In accordance with a second aspect of the invention, this object is achieved by an apparatus for interpreting a data stream having a series of segments with data of a data frame in a series of subsequent data frames, the data frames having more important and less important data, the series of segments having a first segment with an associated first information block, and a second segment. It comprises an error detector for detecting an erroneous segment, and a frame reconstructor for reconstructing data of the data frame by dropping the first information block and collecting the data starting with data from a starting point of the first segment, the starting point of the first segment coinciding with the starting point of the more important data of the data frame.

In accordance with a third aspect of the invention, this object is achieved by a data stream comprising data of a data frame of a series of subsequent data frames, the data frame having more important and less important data, the data stream organized in a series of segments. It comprises a first segment, a second segment and a first information block, the first segment having a starting point coinciding with a starting point of the more important data of the data frame.

In accordance with a fourth aspect of the invention, this object is achieved by a method for generating a data stream having a series of segments using data organized in subsequent data frames, a data frame having more important and less important data. It comprises the following steps: packetising data from a data frame into the series of segments having a first segment and a second segment, where the packetiser is operative to packetise the data of the frame so that a starting point of the more important data coincides with a starting point of the first segment and adding a first information block to the first segment.

In accordance with a fifth aspect of the invention, this object is achieved by a method for interpreting a data stream having a series of segments with data of a data frame in a series of subsequent data frames, the data frames having more important and less important data, the series of segments having a first segment with an associated first information block, and a second segment.

It comprises the following steps: detecting an erroneous segment, interpreting the first information block and extracting information about the starting point of the data frame and extracting information about the order of the data in the series of segments and reconstructing data of the data frame by dropping the first information block and collecting the data starting with data from a starting point of the first segment, the starting point of the first segment coinciding with the starting point of the more important data of the data frame.

The invention also comprises a computer program for implementing the inventive methods.

In summary, the present invention defines a new, efficient transport format and it has a number of advantages. It lowers the amount of lost data over an error prone channel significantly, and is especially suitable for transmitting compressed audio data. This is achieved by adding additional information to each segment that is transmitted over the error-prone channel and by a re-ordering of the data, which has the advantage that the most important information like the Side Info data, which is essential to re-construct the whole frame (see also below at FIG. 7), is located in a single segment and hence decreases significantly the likelihood of losing a whole frame in the case that only a single segment is lost.

Further embodiments of the present invention provide information about a data frame number by assigning different counter values to different data frames. By interpreting the counter values, the number of lost data frames can be identified. Thereby, the problem of wrong time-synchronization is greatly reduced.

In further embodiments of the present invention, the information blocks carry information indicating entry points for resuming to interpret the data output. Preferably, these entry points are the first code words of a beginning scale factor band. The scale factor bands define scale values for a region in the spectral representation and contain spectral values of the frame encoded into code words, which are sorted in ascending order of their corresponding frequency values. The information about the entry point contains an offset into the data stream, where a new scale factor band starts. By choosing these entry points, the overhead is lowered, since less information has to be transmitted. Basically, other code words can also be taken, but then further information has to be transmitted about which code word in which scale factor band represents the entry point. In a very efficient coding the information blocks comprise only a single byte or very few bytes.

In the example of data frames representing compressed audio frames, well-known procedures are concealments by interpolating the data between intact audio frames or to replace the erroneous part by a noise signal or simply to mute the output. The concrete choice depends on the situation, e.g. whether a noise replacement is tolerable or whether enough resources are available to perform a sophisticated interpolation algorithm. The most significant advantage of embodiments of the present invention is that, in the best case, an erroneous segment results only in a loss of the data transmitted in the this segment and all remaining data of the frame can be decoded correctly.

BRIEF DESCRIPTION OF THE DRAWINGS

The present invention will now be described by way of illustrated examples. Features of the invention will be more readily appreciated and better understood by reference to the following detailed description, which should be considered with reference to the accompanying drawings, in which.

DESCRIPTION OF PREFERRED EMBODIMENTS

The below-described embodiments are merely illustrative for the principles of the present invention for improvement of transmitting for example compressed audio over error prone channels with fixed length data segments. It is understood that modifications and variations of the arrangements and the details described herein will be apparent to others skilled in the art. It is the intent, therefore, not to be limited by the specific details presented by way of the description and explanation of embodiments herein.

Figure 1:
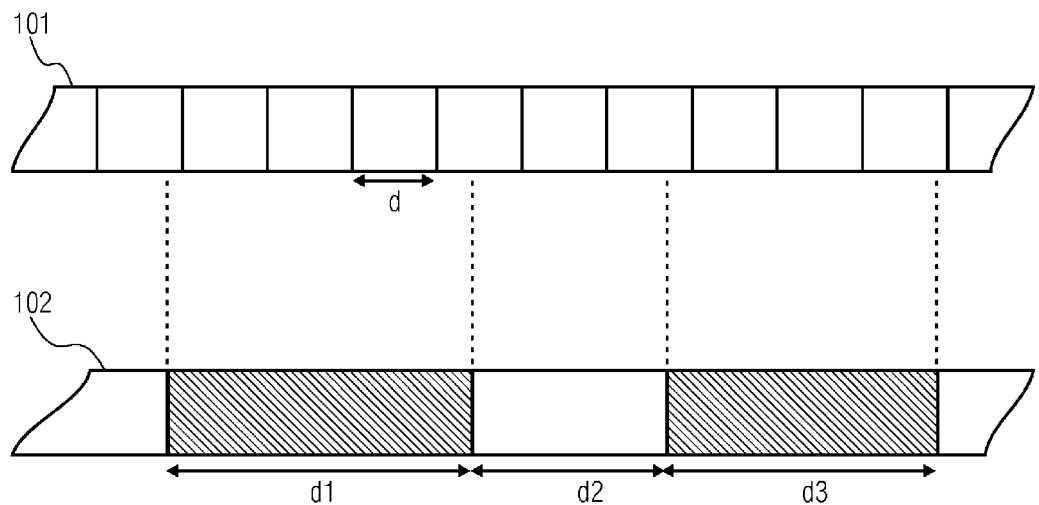
FIG. 1 illustrates the data segments with fixed length and the compressed audio frames with variable length.

FIG. 1 shows compressed data frames with variable lengths, which are transmitted over channels of fixed segment size. In FIG. 1, a data frame d1, a data frame d2 and a data frame d3, which are part of a data stream 102, are shown. In order to transmit them over a channel 101 of fixed segment size, the data frames are split into fixed sized segments of length d. The invention addresses the above mentioned disadvantages of a transmission of compressed audio over error prone channels with fixed length data segments by defining a new, efficient transport format. Specifically, the possibility of losing multiple frames if a segment comprising data of two data frames is damaged during the transmission, which can occur when the transmission is done over an error prone channel with fixed length data segments, is excluded.

Figure 2A:
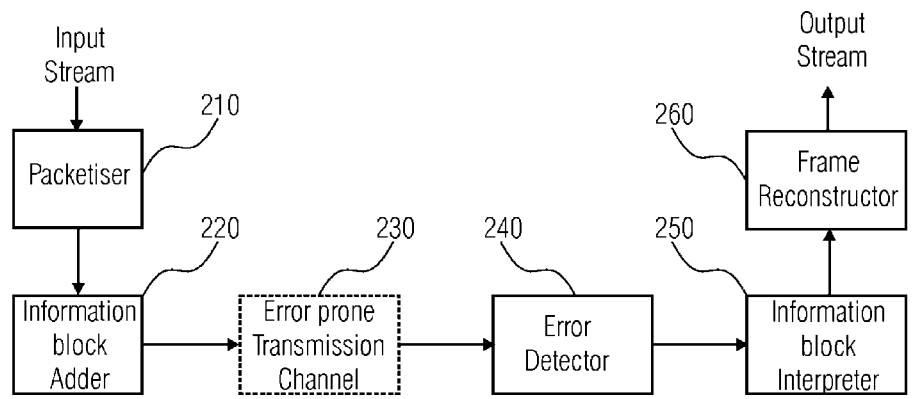
FIG. 2a illustrates the block diagram of a data transmission over the transmission channel with fixed length data segments using the present invention.

FIG. 2a shows schematically a flow of data according to the present invention. The data is first input into a packetiser 210, then sent to an information block adder 220 and after passing an error-prone channel 230, the data enters an error detector 240, which passes the data to an information block interpreter 250 and finally to a frame re-constructor 260, that gives a data output stream. The object of the invention is an apparatus and a method for embedding an input data stream consisting of data frames of variable length, as e.g. compressed audio frames, into the fixed length data segments. Thus, in a first step, the packetiser 210 rearranges the data so that the output of the packetiser 210 are data segments with a fixed size. The information block adder 220 adds an information block to each segment. By transmitting these segments over the error prone transmission channel 230, several segments may get distorted and the error detector 240 identifies the erroneous segments. Information about a transmission error can be obtained either from an underlying transport protocol or from additional control information, which in embodiments of the present invention are added to the data stream. After the erroneous segments have been identified, the information block interpreter 250 reads the information blocks in order to reconstruct as much information as possible from the data stream. This will be explained in more detail at FIG. 3a-3c below. With this information, the frame re-constructor 260 constructs non-corrupt pieces of the original data frames and provides further information about corrupt pieces so that a concealment can be applied to the output stream, e.g. by an audio decoder as will be discussed in more detail in the context of FIG. 4. The preferred size of the segments is fixed by the underlying transport protocol, which typically transfers data by dividing the data stream into segments of fixed size. In other embodiments, the size of the segments can be a multiple of the segment size of the underlying transport protocol. This alternative embodiment has the advantage, that the overhead due to the information blocks is less than for a segment size equal to the segment size of the underlying transport protocol. It has, however, the disadvantage of a possible loss of more data.

Figure 2B:
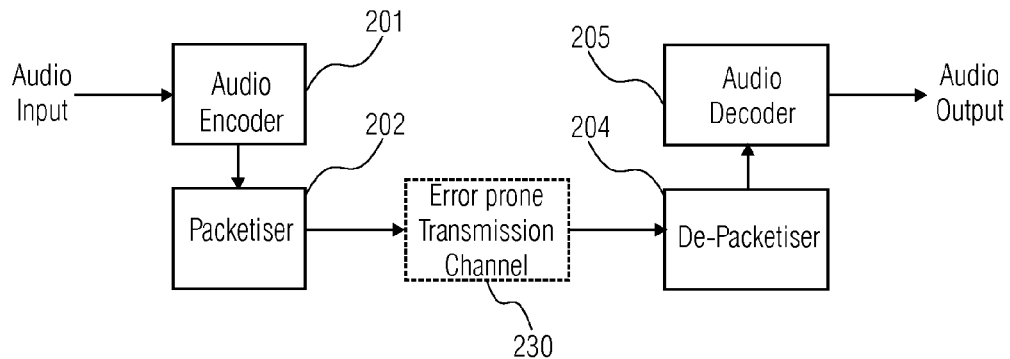
FIG. 2b illustrates the block diagram of a complete audio encoding and decoding chain, including the transmission over the transmission channel with fixed length data segments using the present invention.

FIG. 2b shows the method of embedding of variable length audio frames into a fixed length data segments. A digital audio input signal is fed to an arbitrary audio encoder 201. In a packetiser 202, which comprises in this embodiment the packetiser 210 and the information block adder 220, a compressed audio frame is rearranged and transport information, i.e. the information block, according to the present invention, is added to variable length compressed audio frames. The output of the packetiser 202 is a series of data segments with a fixed size. By transmission of these segments over the error prone transmission channel 230 several segments may get distorted. The de-packetiser 204 strips off the transport information, i.e. the information block according to the present invention, and reorders the bitstream according to its original representation before modification by the packetiser 202. The compressed audio frame is then fed through an audio decoder 205 that calculates one frame of digital audio output samples. Since the audio decoder 205 gets additional information from the de-packetiser 204 on which parts of the bitstream representation of the audio frame that are corrupt, it can do a partial concealment by normal decoding of non-corrupt segments and concealing only the part of the frequency spectrum that corresponds to a corrupt segment.

Figure 3A:
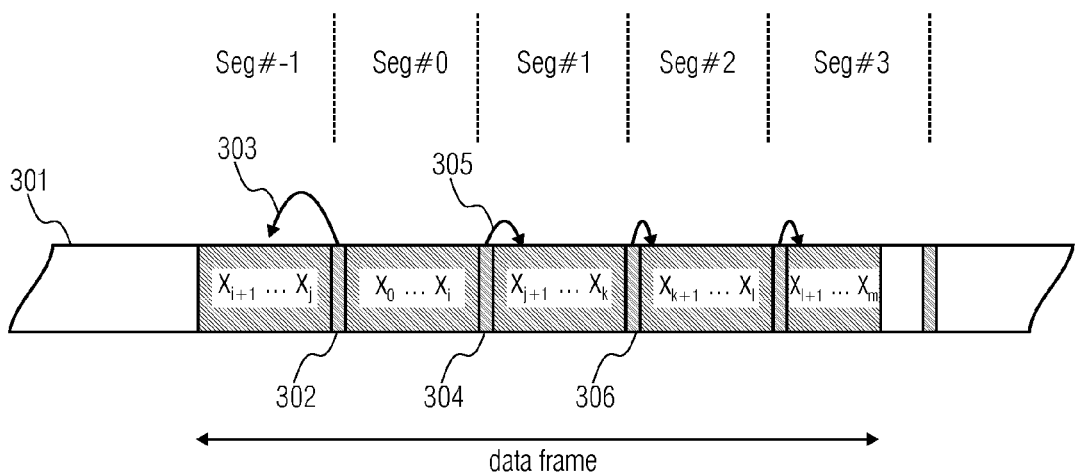
FIG. 3a-3c illustrates an example how information blocks are distributed over multiple data segments, e.g. how one raw audio frame plus the transport information is distributed over multiple data segments, according to the present invention.

FIG. 3a shows an example of a data frame of the data stream 301 and the splitting into different segments. Seg#−1 is the first segment comprising data of the data frame and the remaining data is in this embodiment distributed over the segments: Seg#0 to Seg#3. Each segment has, according to the present invention, a fixed length and has furthermore an information block. The information block of Seg#0 is denoted by 302 and 304 denotes the information block of Seg#1.

The present invention teaches that when the essential data in a data frame, required to be able to decode the rest of the data in a data frame, is stored at a beginning of that frame, this data should be put at the beginning of a new data segment. For compressed audio data, for example, this is the case, i.e. information necessary to reconstruct the audio frame is stored at a beginning of a frame (see FIG. 7 below). Storing the essential data at the beginning of a new data segment ensures that the decoder does not have to conceal two consecutive data frames in case of a single segment loss, as will be clear from the following example.

According to a preferred embodiment of the present invention data of a data frame, sorted in an order $X_0, X_1 \ldots X_m$, starts with a new segment Seg#0 comprising data $X_0 \ldots X_i$ (being the more important data needed to be able to decode the rest of the data in the data frame) and subsequent data are stored according to the following order. Seg#−1 comprises the data $X_{i+1} \ldots X_j$, Seg#1 comprising the data $X_{j+1} \ldots X_k$, Seg#2 comprising the data $X_{k+1} \ldots X_l$ and Seg#3 comprising the remaining data $X_{l+1} \ldots X_m$. (cp. FIG. 3a). This re-ordering avoids the risk of having to conceal two consecutive data frames in case of a single segment loss, since if the Seg#−1 in FIG. 3a is damaged and if the first data stored in a data frame comprises essential information about the data in the data frame, the following segments Seg#C to Seg#3 cannot be decoded correctly.

To distinguish between data segments comprising the start of a new data frame (Seg#0) and succeeding segments comprising additional parts of the data frame (Seg#-1, Seg#1 -#3), the different segment types are signaled, e.g. in the information block 302 and 304, respectively. Since the beginning of the data frame (i.e. the essential information) was put in Seg#0 in FIG. 3a, the Seg#−1 needs to be filled with data following the essential data from the data frame. Hence, the rest of the incomplete previous segment Seg#−1 that has been left over by a previous data frame is filled up with parts of the bit stream data $(X_{i+1} \ldots X_j)$ of the current data frame. An offset pointer 303, contained in the information block 302 of the first segment of the data frame, points to the start of this data in the previous segment Seg#−1. A concrete embodiment of the transmission of compressed audio frames of an aacPlus bitstream over data segments with a fixed length and information blocks comprising eight bits is given below.

In a preferred embodiment of the present invention the information blocks are preceding the raw data stored in each segment and provide an indication of a next possible entry point and an offset pointing to the position belonging to the signaled entry point. This allows for extracting data, e.g. by a decoder that decodes spectral data of an audio frame, even if a previous segment has been corrupted by an erroneous transmission. In FIG. 3a, a pointer 305 gives an example. At the entry points a new interpretable data entity starts. Observing the example where the data stream comprises a stream of compressed audio frames, where the spectral data is coded with code words of variable length, this would require signaling the offset from the start of the segment to the next possible entry point with the precision of one bit. This increases the number of positions to be signaled. However, the present invention teaches that it is not necessary to consider signaling all possible combinations of entry point identifications and entry point offsets. In order to keep a low overhead, also signaling only a subset comprising e.g. the most probable values is possible, which results in a reduction of the number of frames that need to be concealed completely and hence the perceived audio quality is improved compared to prior art methods.

For the case of transmitting compressed audio data, possible entry points are basically any beginning of a new code word. But to keep the overhead as small as possible, in a preferred embodiment, the entry points will be as mentioned above the beginning of a scale factor band and the information blocks will provide information about the scale factor band. If the main issue is to provide a maximum in data error robustness, and the size of a bigger overhead is tolerable, the information blocks can also indicate multiple entry points, that do not necessarily coincide with the beginning of a scale factor band.

In a further embodiment, the information block of Seg#0 has a frame counter value that is increased with every new data frame. This mechanism allows for a re-synchronization in case more segments get lost. The information blocks for the other segments not belonging to the start of the data frame, as e.g. 304, are different from the first segment information block 302.

Figure 3B:
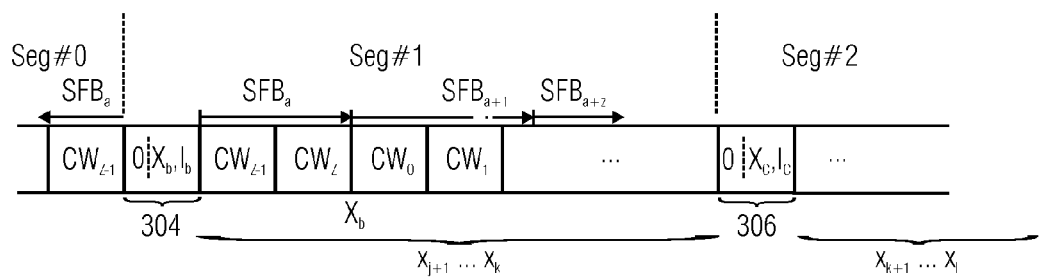
Figure 3C:
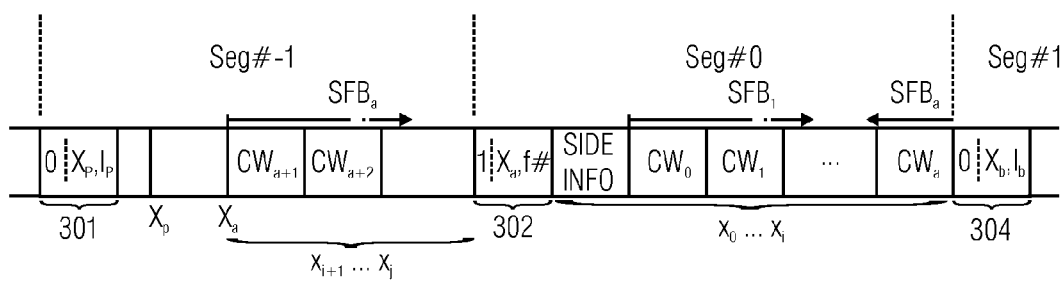

FIG. 3b and FIG. 3c define more clearly the different aspects of the information blocks, for the example that the data frames comprise compressed audio data.

FIG. 3b shows the Seg#1 comprising the data $X_{j+1} \ldots X_k$ with its information block 304 and a part of the Seg# 2 comprising the data $X_{k+1} \ldots X_l$ with the information block 306 and a part of Seg# 0. In this example, the compressed audio data is organized in different scale factor bands (SFB), comprising spectral values of the frame encoded into code words (CW), which are sorted in ascending order to the corresponding frequency values. After the information block 304, the first data in Seg#1 comprises the code word $CW_{z-1}$ and the code word $CW_z$ belonging to the scale factor band $SFB_a$. The remaining code words belonging to this scale factor band are in the preceding segment Seg#0, where the last code word $CW_{z-1}$ is shown. The next scale factor band, $SFB_{a+1}$, with the code words $CW_0, CW_1, \ldots$ starts at the position $X_b$. The information block 304 comprises the information about the starting point of the scale factor band $SFB_{a+1}$, that means the bit value $X_b$ and information $I_b$ to identify the scale factor band. One further bit indicates that the position $X_b$ is a pointer within Seg#1, i.e. it is a forward pointer into the same segment to which is information block is associated. This one-bit signal has in this embodiment the value 0. The next segment, the Seg#2, has an information block 306. This information block contains again the bit value of an entry point $X_c$ in conjunction with the information $I_c$, which identifies the scale factor band to which the entry point belongs, and a one-bit signal, which has the value 0 indicating again that the position $X_c$ is a pointer into the current segment, Seg#2 (this position is not shown in the figure).

FIG. 3c explains in more detail the information block 302, which is the information block of the Seg#0 comprising the data $X_0 \ldots X_i$. This information block is different from all other information blocks belonging to the current data frame. FIG. 3c shows the Seg#0 and Seg#-1 comprising the data $X_{i+1}, \ldots X_j$, and a part of Seg#1. In this embodiment of the present invention, the first data of the data frame is in Seg#0 and starts with a side information block (SIDE INFO) followed by the spectral data, again organized in a subsequent series of scale factor bands comprising spectral values of the frame encoded into code words. The first scale factor band $SFB_1$ comprises the code words $CW_0, CW_1$, etc. The Seg#0 comprises the spectral data up to the code word $CW_a$ belonging to the scale factor band $SFB_a$, and the subsequent code words are included in the Seg#-1, that means starting with a code word $CW_{a+1}$ followed by the code words $CW_{a+2}, \ldots$ In this case, the pointer in the information block 302 does not point to a position within Seg#0, but instead comprises the information about the location $X_a$, where the code words $CW_{a+1}$ starts. The segment Seg.#-1 has an information block 301 comprising a pointer $X_p$, giving the bit value for a starting point of an entry point, and the information $I_p$ identifying the corresponding scale factor band. The spectral data before the point $X_a$ do not belong to the current data frame. The information block 302 comprises moreover a frame counter value f#, which assigns a value to each data frame. In embodiments of the present invention, this frame counter value wraps around after a certain value, i.e. it assigns different counter values only to data frames belonging to a group of data frames. In an example given below, this group of data frames comprises six frames, i.e. this counter value comprises the numbers 0 . . . 5. The information block 302 comprises again a one-bit signal, which identifies this information block as the one comprising pointer to the location in the bit stream after which data of the current frame are stored. Thus, the corresponding pointer points backwards into a preceding segment, the Seg#-1. In the this embodiment, it has the value 1 and hence the information block 302 differs from the information block 304 and all other information blocks (as e.g. 304) within this data frame, where the one-bit signal has the value 0.

Summarizing, in a preferred embodiment of the present invention the transmitted data is compressed audio data and FIG. 3a-3c shows one audio frame embedded together with transport information according to the present invention into the fixed segment length transmission channel. In each segment a small amount of transport information is preceding the raw audio data stored in this segment. In the invention an audio frame always starts with a new segment Seg #0, avoiding the risk of having to conceal two consecutive audio frames in case of a single segment loss. With the transport information 302 and 304 it is possible to distinguish between data segments containing the start of a new audio frame (Seg #0) and succeeding segments containing additional parts of the exemplary compressed audio frame (Seg #1 -#3 ). The distinction is done by signaling the segment type in the transport information 302 resp. 304 (the "0" or "1" values in FIGS. 3b, 3c). The rest of the incomplete previous segment Seg #-1 that has been left over by the previous audio frame is filled up with parts of the bitstream data of the current frame. An offset 303 in FIG. 3a contained in the transport information 302 of the first segment of an audio frame points to the start ($X_a$ in FIG.

3c) of this data in the previous segment Seg #-1. In addition, in the transport information of the segment with the start of the audio frame, there is a small frame counter (f# in FIG. 3c) that is increased with every new audio frame. This mechanism allows for an immediate re-synchronization in case of segments get lost. Because of the frame counter f# the number of lost audio frames is always known, the problem of wrong time-synchronization is greatly reduced. The transport information for the other segments not belonging to the start of the audio frame 304 is different from the first segment transport information 302. An indication ("I" in FIG. 3b) of the next possible entry point and an offset ($X_b$ in FIG. 3b) pointing to the position belonging to the signaled entry point allows the decoder to continue decoding the spectral data even if the previous segment has been corrupt by the erroneous transmission. There might be cases where the spectral data is coded with code words of variable length. This would require signaling the offset from the start of the segment to the next possible entry point bit exact, which increases the number of positions to be signaled. It is not necessary to consider signaling all possible combinations of entry point identification and entry point offset. In order to keep a low overhead, also signaling only a subset comprising the most probable values is possible and results in a reduction of the number of frames that need to be concealed completely and hence improve the perceived audio quality.

Figure 4:
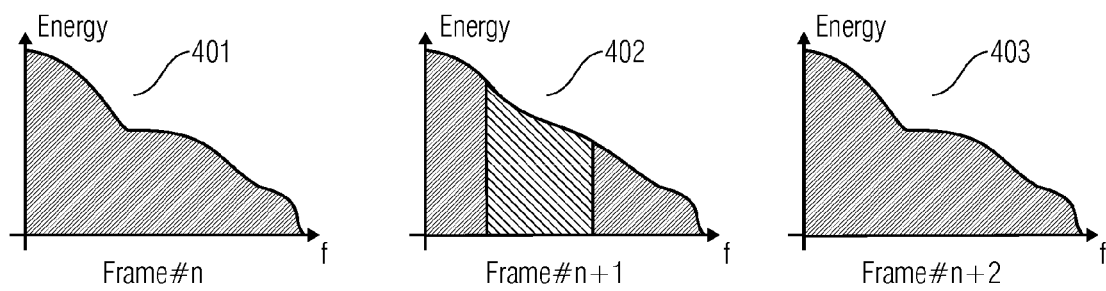
FIG. 4 illustrates the advanced concealment mechanism.

In FIG. 4 the advantage of partial concealment is illustrated. It shows a spectral representation of three consecutive data frames as for example audio frames: a data frame 401, a data frame 402 and a data frame 403. In this example, a data segment in the data frame 402 is lost because of an erroneous transmission, while the previous data frame 401 as well as the next data frame 403 are error-free. Usually, either the whole data frame 402 is lost or in the best case all spectral data after the position in the spectrum corresponding to the lost data segment is not available and has to be estimated. According to embodiments of the present invention, the additional information about possible entry points for extracting of data, as e.g. the decoding of spectral data, allows to skip the corrupt segment e.g. during decoding, losing only a small part of the data (e.g. spectral data). With help of the known data (e.g. spectral data) of the previous data frame 401 and the following data frame 403, a replacement for the missing part of the spectral data has to be calculated by an error concealment algorithm. In the example of data frames representing compressed audio frames, well-known procedures are concealments by interpolating the data between intact audio frames or to replace the erroneous part by a noise signal or simply to mute the output. The concrete choice depends on the situation, e.g. whether a noise replacement is tolerable or whether enough resources are available to perform a sophisticated interpolation algorithm.

Figure 5:
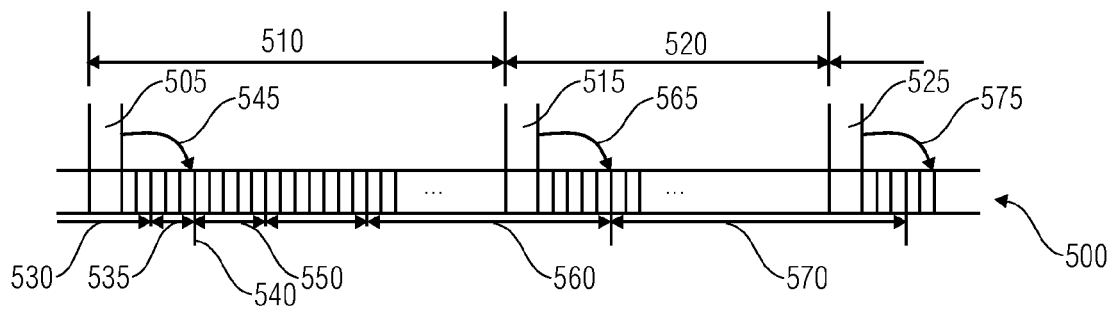
FIG. 5 illustrates two subsequent segments with information blocks and the data entities.

FIG. 5 shows an embodiment for a digitalized data stream 500, where the information blocks carry information about possible entry points. It comprises a segment 510 with an information block 505, another segment 520 with an information block 515 and a following segment has an information block 525. The information in the data stream 500 is organized in code words, a first code word 530 is not completely depicted, since it starts in a preceding segment, a next code word is 535, followed by a code word 550, a code word 560 extends over the segment boundary of the segments 510 and 520, and the last depicted code word is a code word 570, which starts in segment 520 and extends to the following segment (not shown in FIG. 5). In embodiments of the invention, the information block 505 carries information about possible entry points for the case that the preceding segment has been lost so that, e.g. a decoder can resume decoding of data. In the preferred embodiment the information in the information block does not point to a first code word in a given segment, but instead to a first code word at a beginning of a scale factor band, see discussion in the context of FIG. 3b and FIG. 3c. In the example shown in FIG. 5, the scale factor band starts at a point 540 and the information block has a pointer 505 to the entry point representing data of a new scale factor band. In the information block 515 of the segment 520, a pointer 565 points to the entry point, where the code word 570 begins. Again, this entry point represents preferably a starting point of a scale factor band, i.e. the bit in the data stream, where a new scale factor band starts. In the example depicted in FIG. 5, the code word 570 extends into the following segment and the information block 525 gives a pointer 575, where this code word ends and a new one begins.

Figure 6:
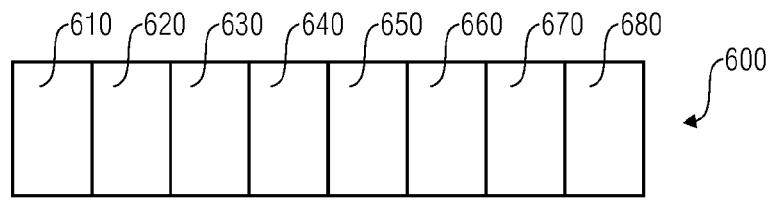
FIG. 6 shows an information block comprising eight bits.

FIG. 6 shows an example of an information block 600 comprising eight bits 610 . . . 680. One of these bits, for example 610, will signal whether the remaining bits, 620 . . . 680, carry information about the starting point of the data frame or whether the remaining bits, 620 . . . 680, carry information about possible entry points, i.e. define pointers into the segment. If the size of the segment as measured in bits is bigger than seven bits, there are certain positions of possible entry points that cannot be coded in the information block. Thus, it can occur that for special segments, no entry points can be defined. A concrete realization of such an information block is given below.

Figure 7:
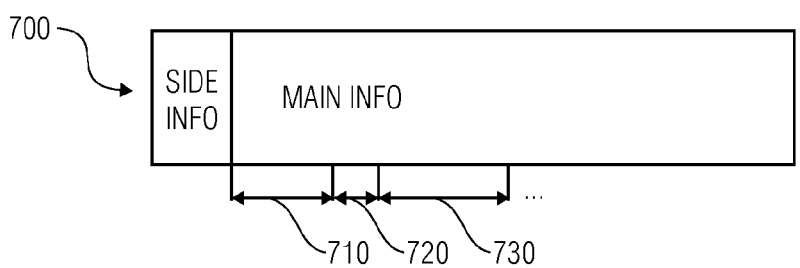
FIG. 7 gives a schematic view on an encoded audio frame.

FIG. 7 gives a schematic view on a data frame 700 that has been generated by an audio encoder as e.g. MPEG HE aac. In such case, each data frame from an audio encoder comprises a Side Info data, which includes essential information necessary for the decoder to interpret the data frames correctly as e.g. the coding format and code lookup tables that combine the values of a certain scale factor band index indicating the start scale factor band of the succeeding spectral data. This Side Info data is located at the beginning of the data frame, followed by the main information part, which contains the spectral data encoded into code words of variable length and grouped into different scale factor bands containing spectral values of the frame, which are rescaled with a scale value and encoded into code words, which are sorted in an ascending order of the corresponding frequency values. In FIG. 7 only three code words are shown, a code word 710, a code word 720, and a code word 730.

In summary, the present invention defines a new, efficient transport format. It lowers significantly the amount of lost data over an error prone channel and is especially suitable for transmitting compressed audio data. A re-ordering of the data is done, which has the advantage that the most important information like the Side Info data, which is essential to re-construct the whole frame, is located in a single segment and hence decreases the likelihood of losing a whole frame. In further embodiment additional information to each segment is added that is transmitted over the error-prone channel and this information indicates entry points for resuming to interpret the data output. Preferably, these entry points are the first code words of a beginning scale factor band. The scale factor bands define scale values for a region in the spectral representation and contain spectral values of the frame encoded into code words, which are sorted and the order of the code words is given by an order of the spectral values sorting form a lowest value followed by subsequent higher values. The information about the entry point gives the bit of the data stream where a new scale factor band starts, and which scale factor band it is. By choosing these entry points, the overhead is lowered, since less information has to be transmitted. Basically, other code words can also be taken, but then further information has to be transmitted in order to identify the code word within the scale factor band. In a very efficient coding the information blocks comprise only a single byte or very few bytes. With the low overhead, it may not be possible to indicate all entry points or only certain positions of entry points can be indicated. E.g. if the number of bits of the information block is small, only positions in a part of a segment can be indicated. In the cases, that no entry points can be given, the information block remains empty or an escape value is given.

Embodiments of the invention provide furthermore information about a data frame number by assigning different counter values to different data frames. By interpreting the counter values, the number of lost data frames can be identified. Thereby, the problem of wrong time-synchronization is greatly reduced.

In further embodiments, the information blocks comprise additional redundancy information, in order to identify erroneous segments after the transmission. This can be, e.g., CRC, parity bits, etc. This error detection is in addition to the usual error detection mechanisms of the underlying transport protocol, as e.g. ADTS or LOAS. In addition, in preferred embodiments the size of the information blocks, as measured in bits, is fixed for all information blocks. Since the segment size is also fixed in preferred embodiments, this means that also the data stored in each segment has a fixed size.

In the example of data frames representing compressed audio frames, well-known procedures are concealments by interpolating the data between intact audio frames or to replace the erroneous part by a noise signal or simply to mute the output. The concrete choice depends on the situation, e.g. whether a noise replacement is tolerable or whether enough resources are available to perform a sophisticated interpolation algorithm. By interpreting the counter values of intact frames, multiple erroneous frames can be identified and an error concealment for the multiple erroneous frames can be applied. The error concealment can be performed either for the compressed audio data, e.g. by replacing the corresponding code words, or after decoding by replacing the erroneous parts of the corresponding audio signals.

The most significant advantage of embodiments of the present invention is that, in the best case, an erroneous segment results only in a loss of the data transmitted in the this segment and all remaining data of the frame can be reconstructed by employing a error concealment.

In other embodiments, the size of the segments can be a multiple of the segment size of the underlying transport protocol. This alternative embodiment has the advantage, that the overhead due to the information blocks is less than for segment size equal to the size of the segment size of the underlying transport protocol. It has, however, the disadvantage of a possible loss of more data.

To further clarify the above-described invention in a further embodiment, the transmission of compressed audio frames of an aacPlus bitstream over data segments with a fixed length is described in detail. In the example the length of a data segment is 168 Bits and a new segment arrives every 20 ms. Thus the overall data rate is 168 bits/20 ms=8400 bit/s. Each 20 ms a segment starts with a one byte information block. An aacPlus audio frame always starts right after the information block with the aacPlus Side Info data (including the side info data needed to decode the AAC spectral data). The aacPlus side info data is followed by the AAC spectral data. The spectral data is ordered from the 0 spectrum line up the maximum spectral line.

If a 20 ms segment comprising the aacPlus side info was lost, the entire audio frame would need to be concealed by the aacPlus decoder. If however one of the 20 ms segments not comprising the aacPlus Side Info data is lost, only parts of the spectrum would have to be concealed. This is possible because the information block includes information to specify the part of the spectrum that is covered by that 20 ms segment.

The structure of an data segment is shown in Table 1 and Table 2 shows the structure of an information block. The description of the solution by means of pseudo code:

TABLE 1

Structure of one 20 ms segment

|  | NBits | Notes |
| --- | --- | --- |
| segment( ) { | | |
| transport_header ( ) | 8 | |
| raw_payload ( ) | 160 | |
| } | | |

TABLE 2 transport Header ( )

|  | Nbits | Notes |
| --- | --- | --- |
| if (audio_frame_start) { | 1 | |
| framecnt_offset_code | 7 | |
| } | | |
| else { | | |
| scfb_offset_code [seg] | 7 | The choice of the code table is dependent on the segment, counted from the first segment of the current frame |
| } | | |

The expressions in the Tables comprise the following information.

raw_payload( ) contains raw aacPlus audio payload data. The de-multiplexer shall concatenate the raw payload chunks belonging to one audio frame and pass on the complete raw audio frame to the aacPlus decoder.

transport_header( ) contains all information needed for the de-multiplexer to identify audio frame boundaries and in case of transmission errors the number of missing audio frames and the parts of the missing spectrum. Information on the missing data shall be passed on to the decoder in order to steer the advanced concealment algorithm.

audio_frame_start is a flag to indicate the start boundary of an aacPlus audio frame, i.e. if this value is for example true, it represents an information block for Seg.#0 (see FIG. 3a) and if this value is for example false, the information block belongs to one of the remaining segments of the data frame.

framecnt_offset_code is a code that combines the values of a aacPlus frame counter value framecnt ranging from 0-5 and an offset value ranging from 0-20. The code is added, for example, to the information block 302 is calculated by the following formula:

code=21×framecnt+offset.

With the above-mentioned range for the framecnt and for the offset, the code has 126 possible values, which can be encoded by seven bits assigned to framecnt_offset_code in the information blocks. The aacPlus audio frame sequence counter value allows specifying the number of missed audio frames. It is increased by one for each audio frame. The audio frame counter framecnt is wrapped around at a value of 6, i.e. the max value is 5. The offset value points to the spectral data content of the previous 20 ms segment. It points in backward direction with a value given in bytes, an offset value of 0 indicates that the previous 20 ms segment did not contain any spectral data belonging to this audio frame.

scfb_offset_code [seg] are added, for example, to the information block 304 are specified by code lookup tables that combine the values of a certain scale factor band index indicating the start scale factor band of the succeeding spectral data plus an offset pointer to the spectral data content of the current segment. The code lookup tables depend on the number of the segment following an audio frame start segment. The code refers to the spectral data contained in the same data segment. The offset points in forward direction with a value given in bits, an offset of 0 indicates that no offset is present. If the combination start scale factor band index and offset value cannot be coded because the value is not contained in the lookup tables, an escape value will be used to indicate that the current data segment cannot be decoded and the according spectrum range needs to be concealed.

For the preferred embodiment of the transmission of compressed audio data, the invention can be summarized as follows.

The invention provides a method for storage or transmission of data with the following steps. Data frames of variable frame size coming from a continuously sending source are packaged into segments which are on average smaller or equal in size than the data frames, all segments have same size and are on average or always smaller or equal in size than the data frames. Then, all segments carry information to signal the beginning of the frame and use additional information to signal that a previous segment contains a part of the current frame. The information about erroneous segments is either given by an underlying transport or storage mechanism or ensured by adding redundancy to the segments e.g. CRC, parity bits, etc.

In addition, further information about the timing or replay order of the frames, e.g. a sequence number, which wraps around can be given.

The most important information is preferably concentrated in a single or only a few bytes.

Segments, which do not contain the beginning of a frame, carry additional information, which guide the drain of the data stream to decode the data in the current segment even if a segment was lost during transmission or storage.

The additional information used to guide the drain of the data stream to decode the data in the current segment even if a segment was lost during transmission or storage is only added for the cases with the highest likelihood to reduce transport overhead.

The additional information embedded during the process is coded for redundancy reduction e.g. using adaptive code tables, combining multiple symbols into a single code word, using Huffman coding or similar.

The data source can be transform based audio codec, which may or may not use bandwidth extension The decoder can use the information about erroneous segments to apply concealment to the missing parts of the signal only.

The whole packaging method does not need any knowledge of the data to be transmitted, the information added is taken from the encoder and passed to the decoder.

Therefore, the present invention comprises a transport mechanism, which allows to package compressed data with variable frame lengths into fixed length data segments. It provides signaling means to apply partial concealment of an audio spectrum in case of transmission errors while adding only a very low transport overhead. It allows for a quick resynchronization at the decoder in case of transmission errors with an accurate time alignment. It also adds preventions for error propagation. The present invention does not demand changes in the raw compressed data format such that a low complexity and "simple design" solution can be achieved.

Depending on certain implementation requirements of the inventive methods, the inventive methods can be implemented in hardware or in software. The implementation can be performed using a digital storage medium, in particular a disk or a CD having electronically readable control signals stored thereon, which cooperate with a programmable computer system such that the inventive methods are performed. Generally, the present invention is, therefore, a computer program product with a program code stored on a machine readable carrier, the program code being operative for performing the inventive methods when the computer program product runs on a computer. In other words, the inventive methods are, therefore, a computer program having a program code for performing at least one of the inventive methods when the computer program runs on a computer.

The invention claimed is:

1. An apparatus for generating a data stream having a series of segments using data organized in subsequent data frames, a data frame having more important and less important data, comprising:
a packetiser for packetising data from a data frame into the series of segments having a first segment, a second segment, and a third segment preceding the first segment, where the packetiser is operative to store data according to the following order:
to packetise the data of the frame into the first segment so that a starting point of the more important data coincides with a starting point of the first segment;
to packetise an amount of data from the frame into the third segment; and
to packetise subsequent frame data following the amount of data into the second segment; and
an information block adder for adding a first information block to the first segment, where the information block adder is operative to add information on a location, at which the amount of data in the third segment begins, to the first information block,
wherein the apparatus for generating a data stream is a hardware apparatus,
wherein a frame includes scale factors and weighted spectral values corresponding to original spectral values weighted by the scale factors, and
wherein the packetiser is operative to packetise the frame such that all scale factors of the frame are included in the first segment, and data included in the third segment or the second segment include weighted spectral values.

2. The apparatus according to claim 1, where the importance of the data is higher, when a loss of data results in distortions, which are more recognizable than distortions caused by a loss of less important data.

3. The apparatus according to claim 1, in which the frames have variable lengths, the segments have a fixed length, and a frame has a starting point and frame data, where the more important frame data begins at the starting point,
wherein the packetiser is operative to packetise the frame so that the starting point of the frame coincides with a starting point of the first segment, to packetise such an amount of data from the frame, which follows the frame data in the first segment into the third segment preceding the first segment until the preceding third segment is full.

4. The apparatus according to claim 1,
in which the second segment has interpretable data entities and a data entity fragment, the data entity fragment including only a part of an interpretable data entity preceding an interpretable data entity, and
wherein the information block adder is operative to add an information block associated to the second segment, the information block indicating an entry point into the second segment, the entry point indicating a start of the interpretable data entity following the data entity fragment.

5. The apparatus according to claim 4,
in which the subsequent data frames include a further data frame,
in which the packetiser is operative to packetise further data frames into a further series of segments, the further series of segments having a first segment and a second segment, the second segment having further interpretable data entities and having a further data entity fragment, the further data entity fragment including only a part of a further interpretable data entity preceding a further interpretable data entity, the further data entity fragment being different from the data entity fragment, and
wherein the information block adder is operative to add a further information block to the second segment of the further series of segments, the further information block indicating an entry point into the second segment of the further series of segments, the further entry point being different from the entry point of the second segment of the series of segments.

6. The apparatus according to claim 1, in which the subsequent data frames include a group of data frames, in which the packetiser is operative to packetise each data frame of the group into a series of segments, each series of segments having a first segment and a second segment,
in which the information block adder is operative to add an first information block associated with a first segment of each data frame, and
in which the information block adder is operative to add a different counter value to the first information block of each data frame.

7. The apparatus according to claim 6, in which the subsequent data frames include a further group of data frames,
in which the packetiser is operative to packetise each data frame of the further group of data frames into a series of segments, and
in which the information block adder is operative to add a different counter value to each first information block of each data frame in the further group,
wherein the information block adder is operative to use the same counter values for the group and the further group of data frames.

8. The apparatus according to claim 6, in which the maximal number of frames in a group is lower or equal to 5, and
in which the information block adder is operative to add a counter value to a first frame of a new group, which is equal to a counter value associated with a first frame of a preceding group.

9. The apparatus according to claim 4,
in which the information block adder is operative to generate the information block such that the information block comprises a plurality of bits, wherein one bit has a first mode value and additional bits of the plurality of bits carry information about the entry point, and
in which the information block adder is operative to generate the first information block such that the first information block has a plurality of bits, one bit having a second mode value, and additional bits carrying information about the starting point of the data frame, the second mode value being different from the first mode value.

10. The apparatus according to claim 1, in which the information block adder is operative to compress the first information block and to add the first information block to the first segment in compressed form.

11. The apparatus according to claim 4, in which the information block adder is operative to compress the information block and to add the information block to the second segment in compressed form.

12. The apparatus according to claim 4, in which the packetiser is operative to packetise data from data frames generated by an audio encoder, and
wherein the information block adder is operative to generate the information block such that the entry point indicates a start of a code word indicating a first spectral value within a scale factor band among a plurality of scale factor bands, the plurality of scale factor bands representing a short time spectrum of an audio signal, and
wherein the information block includes information on a scale factor band index indicating the scale factor band among the plurality of scale factor bands.

13. The apparatus according to claim 1, in which the packetiser is operative to calculate for each segment of the series of segments an additional redundancy information, and
in which the information block adder is operative to add the redundancy information to the information block.

14. The apparatus according to claim 1, in which a data frame includes a stream of data from a start of the frame to an end of the frame,
in which the packetiser is operative to copy at least a portion of data from the data frame into the series of segments, so that data in the segments without the information blocks is identical to at least the portion of data from the data frame.

15. The apparatus according to claim 1, in which the frame includes side information followed by spectral data, the spectral data having code words corresponding to spectral values, the spectral values being sorted in the data frame, so that an order of the code words corresponds to an order of the spectral values, and
in which the packetiser is operative to packetise the frame data such that a segment includes code words defining a spectral range from a first interpretable data entity in the segment to a last interpretable data entity in the segment.

16. An apparatus for interpreting a data stream, the apparatus comprising:
an error detector for detecting an erroneous segment in the data stream having a series of segments with data of a data frame in a series of subsequent data frames, the data frames having more important and less important data, the series of segments having a first segment with an associated first information block, a second segment, and a third segment preceding the first segment, in which the first information block indicates a location in the third segment, the third segment containing data of the data frame starting at the location;

an information block interpreter for interpreting the first information block and extracting information about the location in the third segment at which the data of the data frame begins;

a frame reconstructor for reconstructing data of the data frame by dropping the first information block and collecting the data starting with data from a starting point of the first segment, the starting point of the first segment coinciding with the starting point of the more important data of the data frame, followed by the data of the third segment that follows the location at which data of the data frame begins, followed by data of the second segment, wherein the apparatus for interpreting a data stream is a hardware apparatus, wherein a frame includes scale factors and weighted spectral values corresponding to original spectral values weighted by the scale factors, and wherein the frame reconstructor is operative to reconstruct the frame by extracting scale factors of the frame from the first segment, and by extracting data included in the third segment or in the second segment, wherein the data include weighted spectral values.

17. The apparatus according to claim 16, where the importance of the data is higher, when a loss of data results in distortions, which are more recognizable than distortions caused by a loss of less important data.

18. The apparatus according to claim 16, in which the frame reconstructor is operative to reconstruct data from segments having a fixed length and data frames having variable lengths.

19. The apparatus according to claim 16, in which a series of segments has a fourth segment with an associated information block, in which the error detector is operative to detect an error in a preceding segment and the information block indicating an entry point into the fourth segment, the entry point indicating a start of an interpretable data entity following a data entity fragment, the data entity fragment including only a part of an interpretable data entity preceding the interpretable data entity, in which the information block interpreter is operative to interpret the information block and extracting information about the entry point, and in which the frame reconstructor is operative to drop the erroneous segment and the interpretable data entity fragment and apply an error concealment, the error concealment implying a replacement of the dropped data by other interpretable data.

20. The apparatus according to claim 16, in which the series of segments has a further segment with a further associated information block, in which the error detector is operative to not detect an error in the further segment, and in which the frame re-constructor is operative to reconstruct data from the further segment by dropping the further information block and adding the data of the further segment to the data of the data frame.

21. The apparatus according to claim 16, in which the information block interpreter has stored a fixed segment size and a fixed information block size, in which the first segment and the second segment have the same fixed segment size and the same fixed information block size.

22. The apparatus according to claim 16, in which the data stream having different series of segments with different first segments with associated different first information blocks, the different first information blocks having counter values, in which the information block interpreter is operative to read different counter values in the different first information blocks and use the counter values to order the data frames in a group of data frames.

23. The apparatus according to claim 22, in which the error detector is operative to detect errors in at least two data frames, and in which the frame re-constructor is operative to apply an error concealment for the at least two data frames by using an order as given by the counter values of at least one data frame, which are detected as error free.

24. The apparatus according to claim 19, in which the information block comprises a plurality of bits, wherein one bit has a first mode value and additional bits of the plurality of bits carry information about the entry point, and the first information block has a plurality of bits, one bit having a second mode value, and additional bits carrying information about the starting point of the frame, the first mode value being different from the second mode value; and in which the frame re-constructor is operative to read the one bit of an information block and to interpret the additional bits of the information block depending on a value of the one bit.

25. The apparatus according to claim 19, in which the information block or the first information block is compressed, and in which the information block interpreter is operative to decompress the compressed information block or to decompress the compressed first information block.

26. The apparatus according to claim 19, in which the entry point indicates a code word indicating a first spectral value within a scale factor band among a plurality of scale factor bands, the plurality of scale factor bands representing a short time spectrum of an audio signal, in which the frame re-constructor is operative to reconstruct data of the data frame being an encoded audio signal, and in which the information block interpreter is operative to obtain the entry point and the scale factor band index from the information block, and in which the frame re-constructor is operative to arrange the data in the segment based on the scale factor bands index within the frame and to forward the data frame to an audio decoder.

27. The apparatus according to claim 16, in which the information block includes an additional redundancy information, and in which the error detector is operative to read the additional redundancy information in order to identify an erroneous segment.

28. The apparatus according to claim 26, in which a segment of the series of segments includes code words defining a spectral range from a first interpretable data entity in the segment to a last interpretable data entity in the segment, and in which the frame re-constructor is operative to reconstruct the frame including side information followed by spectral data, the spectral data having code words corresponding to spectral values, the spectral values being sorted in the data frame, so that an order of the code words corresponds to an order of the spectral values.

29. A method for generating an audio data stream having a series of audio data segments using data organized in subsequent data frames, a data frame having more important and less important data, the method comprising:

a computer packetising audio data from an audio data frame into the series of audio data segments having a first audio data segment, a second audio data segment, and a third audio data segment preceding the first audio data segment, so that a starting point of the more important data coincides with a starting point of the first audio data segment, followed by packetising an amount of audio data from the data frame into the third audio data segment, followed by packetising subsequent audio data following the amount of audio data into the second audio data segment;

the computer adding a first information block to the first audio data segment wherein a frame includes scale factors and weighted spectral values corresponding to original spectral values weighted by the scale factors, and wherein the frame is packetized such that all scale factors of the frame are included in the first segment, and data included in the third segment or the second segment include weighted spectral values.

30. A method for interpreting a data stream, the method comprising:

a computer detecting an erroneous audio data segment in the data stream having a series of audio data segments with data of a data frame in a series of subsequent data frames, the data frames having more important and less important data, the series of audio data segments having a first audio data segment with an associated first information block, and a second audio data segment, and a third audio data segment preceding the first audio data segment, in which the first information block indicates a location in the third audio data segment, the third audio data segment containing data of the data frame starting at the location;

the computer interpreting the first information block, extracting information about the starting point of the data frame, extracting information about the location in the third audio data segment at which the data of the data frame begins, and extracting information about the order of the data in the series of audio data segments; and the computer reconstructing data of the data frame by dropping the first information block and collecting the data starting with data from a starting point of the first audio data segment, the starting point of the first audio data segment coinciding with the starting point of the more important data of the data frame, followed by data of the third audio data segment that follows the location at which data of the data frame begins, followed by reconstructing data of the second segment, wherein the method is implemented by a hardware apparatus wherein a frame includes scale factors and weighted spectral values corresponding to original spectral values weighted by the scale factors, wherein the frame is reconstructed by extracting scale factors of the frame from the first segment, and by extracting data included in the third segment or in the second segment, wherein the data include weighted spectral values, and wherein the method is implemented by a hardware apparatus.

31. A non-transitory digital storage medium having stored thereon a computer program with a program code to execute the method according to claim 29 or claim 30, if the computer program is executed on a computer.

32. An apparatus for generating a data stream having a series of segments using data organized in subsequent data frames, a data frame having more important and less important data, comprising:

a packetiser for packetising data from a data frame into the series of segments having a first segment, a second segment and a third segment preceding the first segment, where the packetiser is operative to store data according to the following order to packetise the data of the frame into the first segment so that a starting point of the more important data coincides with a starting point of the first segment;

to packetise an amount of data from the frame into the third segment; and to packetise subsequent frame data following the amount of data into the second segment; and an information block adder for adding a first information block to the first segment, where the information block adder is operative to add information on a location, at which the amount of data in the third segment begins, to the first information block, wherein the subsequent data frames include a group of data frames, wherein the packetiser is operative to packetise each data frame of the group into a series of segments, each series of segments having a first segment and a second segment, wherein the information block adder is operative to add a first information block associated with a first segment of each data frame, wherein the information block adder is operative to add a different counter value to the first information block of each data frame, wherein the maximal number of frames in a group is lower or equal to 5, and wherein the information block adder is operative to add a counter value to a first frame of a new group, which is equal to a counter value associated with a first frame of a preceding group.

33. An apparatus for interpreting a data stream, the apparatus comprising:

an error detector for detecting an erroneous segment in the data stream having a series of segments with data of a data frame in a series of subsequent data frames, the data frames having more important and less important data, the series of segments having a first segment with an associated first information block, a second segment, and a third segment preceding the first segment, in which the first information block indicates a location in the third segment, the third segment containing data of the data frame starting at the location;

an information block interpreter for interpreting the first information block and extracting information about the location in the third segment at which the data of the data frame begins;

a frame reconstructor for reconstructing data of the data frame by dropping the first information block and collecting the data starting with data from a starting point of the first segment, the starting point of the first segment coinciding with the starting point of the more important data of the data frame, followed by the data of the third segment that follows the location at which data of the data frame begins, followed by data of the second segment, wherein a series of segments has a fourth segment with an associated information block, wherein the error detector is operative to detect an error in a preceding segment and the information block indicating an entry point into the fourth segment, the entry point indicating a start of an interpretable data entity following a data entity fragment, the data entity fragment including only a part of an interpretable data entity preceding the interpretable data entity, wherein the information block interpreter is operative to interpret the information block and extracting information about the entry point, and wherein the frame reconstructor is operative to drop the erroneous segment and the interpretable data entity fragment and apply an error concealment, the error concealment implying a replacement of the dropped data by other interpretable data.

34. A method for generating an audio data stream having a series of audio data segments using data organized in subsequent data frames, a data frame having more important and less important data, the method comprising:

packetising audio data from an audio data frame into the series of audio data segments having a first audio data segment and a second audio data segment and a third audio data segment preceding the first audio data segment, so that a starting point of the more important data coincides with a starting point of the first audio data segment, followed by packetising an amount of audio data from the data frame into the third audio data segment, followed by packetising subsequent audio data following the amount of audio data into the second audio data segment; and adding a first information block to the first audio data segment;

wherein the subsequent data frames include a group of data frames, wherein each data frame of the group is packetized into a series of segments, each series of segments having a first segment and a second segment, wherein a first information block associated with a first segment of each data frame is added, and wherein a different counter value is added to the first information block of each data frame, wherein the maximal number of frames in a group is lower or equal to 5, and wherein a counter value is added to a first frame of a new group, which is equal to a counter value associated with a first frame of a preceding group.

35. A method for interpreting a data stream, the method comprising:

detecting an erroneous audio data segment in the data stream having a series of audio data segments with data of a data frame in a series of subsequent data frames, the data frames having more important and less important data, the series of audio data segments having a first audio data segment with an associated first information block, and a second audio data segment, and a third audio data segment preceding the first audio data segment, in which the first information block indicates a location in the third audio data segment, the third audio data segment containing data of the data frame starting at the location;

interpreting the first information block and extracting information about the starting point of the data frame and extracting information about the location in the third audio data segment at which the data of the data frame begins and extracting information about the order of the data in the series of audio data segments; and reconstructing data of the data frame by dropping the first information block and collecting the data starting with data from a starting point of the first audio data segment, the starting point of the first audio data segment coinciding with the starting point of the more important data of the data frame, followed by data of the third audio data segment that follows the location at which data of the data frame begins, followed by reconstructing data of the second segment, wherein a series of segments has a fourth segment with an associated information block, wherein an error in a preceding segment and the information block indicating an entry point into the fourth segment is detected, the entry point indicating a start of an interpretable data entity following a data entity fragment, the data entity fragment including only a part of an interpretable data entity preceding the interpretable data entity, wherein the information block is interpreted and information about the entry point is extracted, and wherein the erroneous segment and the interpretable data entity fragment are dropped and an error concealment is applied, the error concealment implying a replacement of the dropped data by other interpretable data.

36. A non-transitory storage medium having stored thereon a computer program with a program code to execute the method according to claim 34, if the computer program is executed on a computer.

37. A non-transitory storage medium having stored thereon a computer program with a program code to execute the method according to claim 35, if the computer program is executed on a computer.

* * * * *